United States Patent [19]

Nakanishi et al.

[11] Patent Number: 5,527,904

[45] Date of Patent: Jun. 18, 1996

[54] **POLYSACCHARIDES, PROCESS FOR PRODUCING POLYSACCHARIDES, USES OF POLYSACCHARIDES AND *AZOTOBACTER BEIJERINCKII* TNM1**

[75] Inventors: Osamu Nakanishi, Ibaraki; Yoichi Ooiso, Osaka; Takeshi Okumiya, Yao; Ryosuke Sugihara, Amagasaki; Akira Misaki, Ashiya; Masahira Nakagawa, Takatsuki, all of Japan

[73] Assignee: Tayca Corporation, Japan

[21] Appl. No.: 201,698

[22] Filed: Feb. 25, 1994

[30] Foreign Application Priority Data

| Mar. 1, 1993 | [JP] | Japan | 5-064681 |
| Jul. 29, 1993 | [JP] | Japan | 5-207046 |
| Nov. 15, 1993 | [JP] | Japan | 5-308620 |

[51] Int. Cl.$^6$ ............................................. C12P 19/04
[52] U.S. Cl. ........................................ 536/123.1; 435/101
[58] Field of Search ............................. 536/123.1; 435/101

[56] References Cited

U.S. PATENT DOCUMENTS 3,960,832  6/1976  Kang et al. .............................. 524/47
4,338,432  7/1982  Lawson et al. .......................... 536/123

OTHER PUBLICATIONS

R. Lopez et al., *Microbiologia Espanola*, 21(1):53–75 (1968).
L. Likhosherstov et al., *Carbohydrate Research*, 222:233–238 (1991).
Database WPI, Week 7508, Derwent Publications Ltd.; AN 13382W.
Nitikin "The Chemistry of Cellulose and Wood" Academy of Sciences of the USSR Israel Program for Scientific Translations, Jerusalem 1966, pp. 62–71.

*Primary Examiner*—Nathan M. Nutter
*Attorney, Agent, or Firm*—David G. Conlin; Peter F. Corless

[57] ABSTRACT

Disclosed are novel polysaccharides having the following physicochemical properties: (1) a molecular weight determined by gel filtration chromatography is about $5\times10^3$ to $10\times10^6$, (2) the constituent glycoses are D-galacturonic acid, L-rhamnose and D-glucose, (3) the constituent glycoses are joined substantially by 1,3-linkages, and (4) a configuration of D-galacturonic acid is $\alpha$, that of L-rhamnose is $\beta$ and that of D-glucose is $\alpha$. A process for producing polysaccharides composed of D-galacturonic acid, L-rhamnose and D-glucose, use of the polysaccharides and a strain for producing the polysaccharides are also disclosed.

11 Claims, 2 Drawing Sheets

POLYSACCHARIDES, PROCESS FOR PRODUCING POLYSACCHARIDES, USES OF POLYSACCHARIDES AND *AZOTOBACTER BEIJERINCKII* TNM1

BACKGROUND OF THE INVENTION

The present invention relates to novel polysaccharides, a process for producing polysaccharides, uses of the polysaccharides and a strain producing the polysaccharides. The novel polysaccharides of the present invention may be used in various fields, for example, as a humectant, a film-forming agent, an emulsifier, a foam stabilizer, a water-retaining agent and a cement admixture.

Japanese Patent Application Laid-Open (Kokai) No. 63-156707 (1988) proposes a cosmetic composition containing hyaluronic acid as a humectant. The humectant, when used in cosmetics, serves for mitigating stimulus from the outside and for protecting the skin from becoming rough, and also improves the touch to the skin of the cosmetics. Generally, a humectant used as a cosmetic material is desired to have a moisture retention within the range of 10 to 50% under an ordinary environmental condition with a relative humidity of 40 to 80%. It is also required that its moisture retaining ability should be scarcely affected by the change of relative humidity (Fragrance Journal, special No. 9 "Science of Humectant", 1988, page 34, etc.).

However, hyaluronic acid has a serious defect that its moisture retaining ability is unstable and tends to be influenced by ambient humidity.

As a result of extensive search for a material having excellent moisture retaining ability, the present inventors have found that novel polysaccharides obtained by using a novel microorganism have excellent moisture retaining ability which is hardly influenced by ambient relative humidity. It has been also found that the novel polysaccharides have other useful properties. The present invention has been achieved on the basis of these findings.

SUMMARY OF THE INVENTION

An object of the present invention is to provide novel polysaccharides.

Another object of the present invention is to provide a process for producing polysaccharides and advantageous uses of the polysaccharides.

Still another object of the present invention is to provide a novel microorganism of the genus Azotobacter.

To achieve the aims, in a first aspect of the present invention, there are provided novel polysaccharides having the following physicochemical properties:

(1) a molecular weight determined by gel filtration chromatography is about $5 \times 10^3$ to $10 \times 10^6$, (2) the constituent glycoses are D-galacturonic acid, L-rhamnose and D-glucose, (3) the constituent glycoses are joined substantially by 1,3-linkages, and (4) a configuration of D-galacturonic acid is α, that of L-rhamnose is β and that of D-glucose is α.

In a second aspect of the present invention, there is provided a process for producing polysaccharides, which comprises culturing a microorganism belonging to the genus Azotobacter and having an ability to produce polysaccharides composed of D-galacturonic acid, L-rhamnose and D-glucose, whose constituent glycoses are joined substantially by 1,3-linkages, and collecting the polysaccharides from the culture.

In a third aspect of the present invention, there is provided a humectant comprising polysaccharides which have a molecular weight determined by gel filtration chromatography of about $5 \times 10^3$ to $10 \times 10^6$ and which are composed of D-galacturonic acid, L-rhamnose and D-glucose.

In a fourth aspect of the present invention, there is provided a film forming agent comprising polysaccharides which have a molecular weight determined by gel filtration chromatography of about $5 \times 10^3$ to $10 \times 10^6$ and which are composed of D-galacturonic acid, L-rhamnose and D-glucose.

In a fifth aspect of the present invention, there is provided an emulsion stabilizer comprising polysaccharides which have a molecular weight determined by gel filtration chromatography of about $5 \times 10^3$ to $10 \times 10^6$ and which are composed of D-galacturonic acid, L-rhamnose and D-glucose.

In a sixth aspect of the present invention, there is provided a foam stabilizer comprising polysaccharides which have a molecular weight determined by gel filtration chromatography of about $5 \times 10^3$ to $10 \times 10^6$ and which are composed of D-galacturonic acid, L-rhamnose and D-glucose.

In a seventh aspect of the present invention, there is provided a water-retaining agent comprising polysaccharides which have a molecular weight determined by gel filtration chromatography of about $5 \times 10^3$ to $10' 10^6$ and which are composed of D-galacturonic acid, L-rhamnose and D-glucose.

In an eighth aspect of the present invention, there is provided a cement admixture comprising polysaccharides which have a molecular weight determined by gel filtration chromatography of about $5 \times 10^3$ to $10 \times 10^6$ and which are composed of D-galacturonic acid, L-rhamnose and D-glucose.

In a ninth aspect of the present invention, there is provided a polysaccharide-producing Azotobacter beijerinckii TNM1 (FERM BP-4194) or mutants thereof.

DETAILED DESCRIPTION OF THE INVENTION

The polysaccharides of the present invention are mainly characterized by that they are composed of D-galacturonic acid, L-rhamnose and D-glucose, and that the constituent glycoses are joined substantially by 1,3-linkage [(1→3)-linkages]. There are known various polysaccharides having different combinations of constituent glycoses, but no polysaccharide is known in which the above constituent glycoses are joined substantially by 1,3-linkages.

In the polysaccharides of the present invention, the configuration of D-galacturonic acid is α, that of L-rhamnose is β and that of D-glucose is α, and the molar ratio of the constituent glycoses is as follows:

D-galacturonic acid:L-rhamnose:D-glucose =0.6 to 1:0.8 to 1.2:0.8 to 1.2.

The molecular weight of the polysaccharides determined by gel filtration chromatography is in the range of about $5 \times 10^3$ to $10 \times 10^6$. Specifically, the molecular weight can be the determined by GPC mode high-performance liquid chromatography with an ASAHIPAK GFA-7MF column (mfd. by Asahi Chemical Industry Co., Ltd.) using a 0.1M $NaNO_3$ aqueous solution as mobile phase, based on a molecular weight-retention time standard curve drawn by employing pullulans of known molecular weight as standard.

The polysaccharides of the present invention have the following properties:

(1) Appearance: White, cotton-like (freeze-dried product).

(2) Solubility: Soluble in water, dilute acids, dilute alkalis and DMSO and insoluble in methanol, ethanol and acetone.

Figure 1:
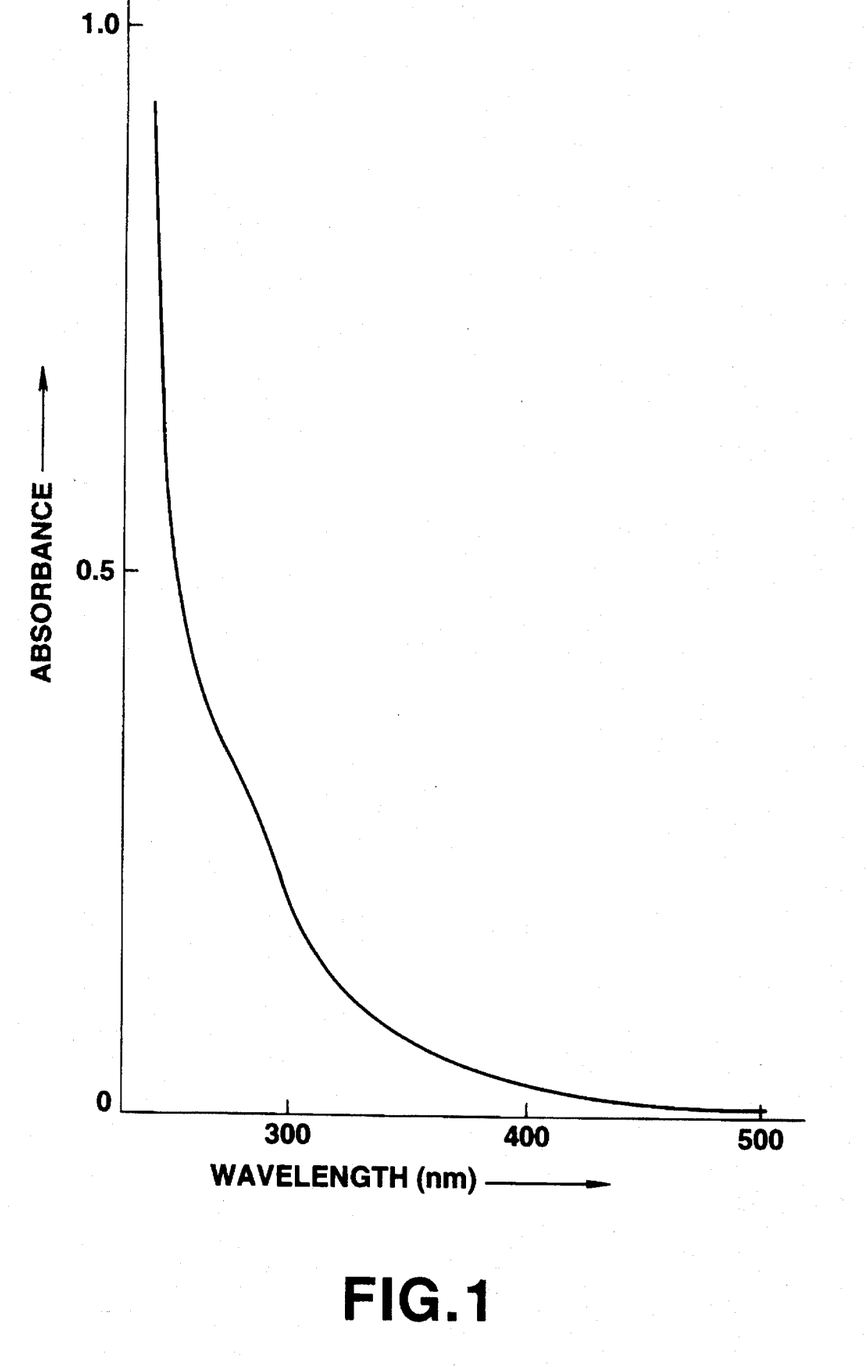
FIG. 1 is an ultraviolet absorption spectrum of the polysaccharides of the present invention.

(3) Ultraviolet absorption spectrum: The spectrum measured by using a quartz cell with light path length of 10 mm at 0.5% (w/v) aqueous solution is shown in FIG. 1. As is seen from FIG. 1, there is observed no absorption at 280 nm peculiar to protein (peptide) and at 260 nm peculiar to nucleic acid.

Figure 2:
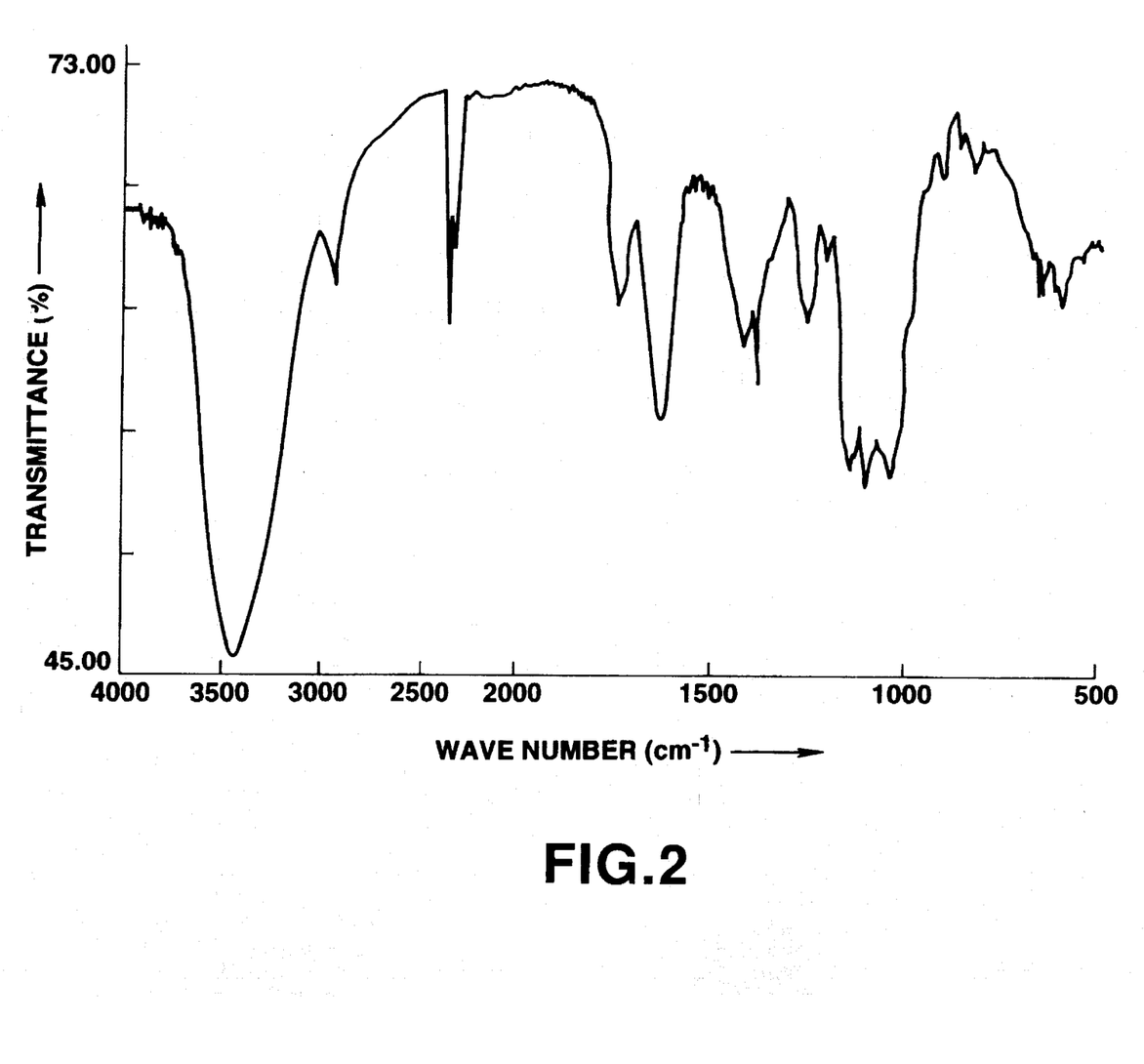
FIG. 2 is an infrared absorption spectrum of the polysaccharides of the present invention.

(4) Infrared absorption spectrum: The spectrum measured by KBr tablet method is shown in FIG. 2. As is seen from FIG. 2, there is observed absorption by hydroxyl group at around 3400 $cm^1$, absorption by carboxyl group of uronic acid at around 1620 $cm^{-1}$, absorption by O-acetyl group at around 1730 $cm^{-1}$, absorptions by ether bond at around 1100 and 1250 $cm^{-1}$ and absorption by alkane group at around 2950 $cm^{-1}$. The sharp absorption band at around 2350 $cm^{-1}$ is due to carbon dioxide in the atmosphere.

(5) Color reactions: Phenol-sulfuric acid method: positive m-Phenylphenol method: positive Elson-Morgan method: negative Positive in phenol-sulfuric acid method indicates the presence of saccharides and positive in m-phenylphenol method indicates the presence of uronic acid. Also, negative in Elson-Morgan method confirms absence of hexosamine. These facts indicate that no amino sugar exists. Thus, it is confirmed that the polysaccharides of the present invention are acidic polysaccharides containing uronic acid.

(6) Constituent glycoses The polysaccharides of the present invention and polysaccharides obtained by reducing the carboxyl group of uronic acid in the polysaccharides were subjected to acid hydrolysis at 100° C. for 6 hours by using 2 M trifluoroacetic acid (TFA), and then alditol acetates were derived therefrom. Each of the obtained derivatives was subjected to gas chromatographic analysis using an ECNSS-M coated column ("Gas Chrom Q" mfd. by Wako Pure Chemicals Co., Ltd.). Compounds identical with the compounds derived from D-galactose, L-rhamnose and D-glucose were detected. Also, acid hydrolysis of the polysaccharides was carried out under the same conditions as above, and after pyridylamino fluorescent labeling, liquid chromatographic analysis was conducted with a "TSK gel Sugar AXI" column (mfd. by Toso Co., Ltd.) using a 1:9 mixed solution of $CH_3CN$ and 0.7 M $K_3BO_3$ (pH 9.0) as mobile phase. The results of these analyses confirm that the polysaccharides of the present invention are composed of D-galacturonic acid, L-rhamnose and D-glucose, and that the molar ratio thereof is as follows:

D-galacturonic acid:L-rhamnose:D-glucose =0.6 to 1.0:0.8 to 1.2:0.8 to 1.2.

(7) Linkages between constituent glycose residues The polysaccharides of the present invention and polysaccharides obtained by reducing the carboxyl group of uronic acid in the polysaccharides were methylated according to Hakomori method and then subjected to acid hydrolysis at 100° C. for 12 hours with 88% HCOOH and for additional 6 hours with 2 M TFA, followed by derivation to alditol acetates. Each of the obtained derivatives was subjected to gas chromatographic analysis using ECNSS-M coated column and "Silicon OV-1" column (mfd. by Wako Pure Chemical Industries, Ltd.) and further to GC-MS analysis using "Silicon OV-1" column. 2,4,6-Tri-O-methyl-D-galactose, 2,4-di-O-methyl-L-rhamnose and 2,4,6-tri-O-methyl-D-glucose were detected. From these facts, it was confirmed that the residues of D-galacturonic acid, L-rhamnose and D-glucose, which are the constituent glycoses of the polysaccharides of the present invention, are joined substantially by 1,3-linkages. It was also tried to conduct perfect Smith degradation of the polysaccharides of the present invention and the polysaccharide obtained by reducing the carboxyl group of the uronic acid, but no perfect Smith degradation occurred. This fact indicates that the residues of D-galacturonic acid, L-rhamnose and D-glucose are joined substantially by 1,3-linkages, or there is a branch point which is not subject to perfect Smith degradation. In view of this fact and the result of the above methylation analysis, it is determined that the residues of D-galacturonic acid, L-rhamnose and D-glucose are joined substantially by 1,3-linkages. Further, as a result of partial acid hydrolysis of the polysaccharides of the present invention, it is found that L-rhamnose is less apt to appear as a monosaccharide in the product than D-glucose. It is known that, generally, a linkage between the uronic acid residue and a neutral sugar residue glycosidic-linked to carbon atom at the 1-position of the uronic acid residue in a polysaccharide is relatively stable to acids. Therefore, it is supposed that the residue glycosidic-linked to carbon atom at the 1-position of D-galacturonic acid in the polysaccharides of the present invention is principally L-rhamnose residue.

(8) Specific rotatory power $[\alpha]^{25}_D=+120°$ (c=0.5, aqueous solution). In view of the above value of specific rotatory power and the fact that the molar ratio of the constituent glycoses is: D-galacturonic acid:L-rhamnose:D-glucose=0.6–1.0:0.8–1.2:0.8–1.2, it is judged that configurations of the respective constituent glycoses are α for D-galacturonic acid and D-glucose and β for L-rhamnose.

From the above properties, the polysaccharides of the present invention are determined to be acidic heteropolysaccharides which are composed of D-galacturonic acid, L-rhamnose and D-glucose, with the molar ratio thereof being: D-galacturonic acid:L-rhamnose:D-glucose= 0.6–1.0:0.8–1.2:0.8–1.2, and in which the residues of the respective constituent glycoses are joined substantially by 1,3-linkages, and the configurations of the constituent glycoses are α for D-galacturonic acid and D-glucose and β for L-rhamnose. The principal repeating unit of the polysaccharides of the present invention is deemed to be [D-galacturonic acid(1→3) L-rhamnose(1→3)D-glucose(1→3)]. Regarding the constituent glycoses, those in which hydroxyl groups are partially substituted with O-acetyl groups are included in the scope of the present invention. Usually, the number of O-acetyl groups is, on the average, 1 or less per one constituent glycose residue. Since no compound which is composed of D-galacturonic acid, L-rhamnose and D-glucose, whose constituent glycoses are joined substantially by 1,3-linkages, can be found among the known substances, the polysaccharides of the present invention are confirmed to be novel acidic heteropolysaccharides.

The process for producing the polysaccharides of the present invention is described below.

The process of the present invention comprises culturing a microorganism belonging to the genus Azotobacter and having an ability to produce polysaccharides composed of D-galacturonic acid, L-rhamnose and D-glucose, whose constituent glycoses are joined substantially by 1,3-linkages, and collecting the polysaccharides from the culture. In a preferred embodiment of the present invention, Azotobacter beijerinckii is used as the polysacharide-producing microorganism, and in a more preferred embodiment of the invention, a strain, Azotobacter beijerinckii TNM1 (FERM BP-4194) isolated from a natural soil or a mutant thereof is used as the polysacharide-producing microorganism. The mutant can be produced by a known mutagenic means, for example, application of radiation such as ultraviolet rays or X-rays or use of a chemical mutagenic compound such as ethyl methanesulfonate (EMS) and N-methyl-N'-nitro-N-nitrosoguanidine (MNNG).

The mycological properties of the Azotobacter beijerinckii TNM1 are shown in Table 1.

TABLE 1

| Mycological properties | |
|---|---|
| Morphology | Rather polymorphic; colony is mucoidal |
| Gram-stain | − |
| Glucose OF | O type |
| Motility | − |
| Flagellum | − |
| Catalase | + |
| Oxydase | + |
| Growth with McConkey's agar | + |
| Growth with SS agar | + |
| Growth with KCN medium | − |
| Citrate utilization | + |
| Nitrate reduction | +$^w$ (weakly positive) |
| Gas generation from nitrate | − |
| Growth with nitrogen-free medium | +$^w$ (weakly positive) |
| Acid generation from carbohydrates: | |
| Glucose | + |
| Lactose | − |
| Maltose | − |
| Mannitol | + |
| Salicin | − |
| Saccharose | + |
| Xylose | + |
| Fructose | + |
| Inositol | − |
| Cellobiose | − |
| Trehalose | + |
| Galactose | + |
| Casein hydrolysis | + |
| Gelatin hydrolysis | + |
| Starch hydrolysis | − |
| Urease | − |
| VP | − |
| Indole | − |
| ONPG | − |
| Lysine decarboxylase | − |
| Arginine dihydrolase | + |
| Ornithine decarboxylase | − |
| Aesculin hydrolysis | − |
| Tween 80 hydrolysis | − |
| LV | + |
| Extracellular polysaccharide productivity | + |

From a comparison of the above mycological properties and the data given in Bergey's Manual of Systematic Bacteriology, Vol. 1, p. 228, 1984, the followings were confirmed:

(1) The strain of the present invention is classified as a mutant TNM1 strain of Azotobacter beijerinckii. Its safety will be ensured as it belongs to the genus Azotobacter.

(2) The above extracellular polysaccharide productivity and casein and gelatin hydrolyzabilities are not noted in the type strain (ATCC 19360), but the strain according to the present invention and the type strain are identical with each other in other properties.

The strain according to the present invention was deposited at the National Institute of Bioscience and Human-Technology, Agency of Industrial Science and Technology, Ministry of International Trade and Industry, Japan under Accession No. FERM BP-4194, on Feb. 18, 1993.

As the medium for culturing the microorganism according to the process of the present invention, it is possible to use any medium in which microorganisms belonging to the genus Azotobacter can grow and which contains appropriate amounts of a carbon source, a nitrogen source, inorganic salts and a micronutrient for producing the polysaccharides of the present invention. As the carbon source, glucose, galactose, fructose, xylose, mannitol, saccharose, trehalose, glucuronic acid, galacturonic acid and the like can be used. As the nitrogen source, synthetic compounds such as nitrates, ammonium salts, urea and the like, natural organic substances such as polypeptone, corn steep liquor, yeast extract, meat extract, de-fatted soybean extract, peptides, amino-acids and the like can be used. As the inorganic salts, phosphates, potassium salts, sulfates, magnesium salts and the like can be used. Iron salts, calcium salts, manganese salts and the like may be added to the medium, if necessary. Yeast extract, various types of vitamin, etc., can be used as micronutrients.

As for the medium used in the present invention, it may be either solid or liquid. In case of a liquid medium, although stationary culture may be employed, shaking culture or submerged culture is preferred as it gives the polysaccharides of the present invention in a higher yield. Culture pH is not restricted as far as it is suited for production of the polysaccharides of the present invention, but usually a pH of 4 to 8 is appropriate. Culture temperature is also not specifically restricted, but usually a temperature of 20° to 35° C. is appropriate. As for culture time, a period in which the yield of the polysaccharides of the present invention is maximized is selected. Usually, a period of 1 to 7 days is appropriate.

A known method may be employed for collecting the polysaccharides of the present invention from the culture obtained by the above-described culture method. For example, firstly, the bacterial cells are removed from the culture by suitable method such as centrifugation or filtration, and then an organic solvent such as methanol, ethanol, isopropanol, acetone and the like is added to the obtained culture medium to produce a precipitate. The collected precipitate is dissolved in water and dialyzed against water, and the dialyzate is dried by an appropriate method such as through-flow drying, hot-air drying, spray drying, drum drying, vacuum drying, freeze-drying, etc., to recover the polysaccharides of the present invention.

It is also possible to employ a method by which the substances other than the polysaccharides of the present invention are removed from the culture medium by means of ultrafiltration, and the resulting enriched solution is dried by suitable means such as mentioned above. Further, if necessary, the product may be purified according to an ordinary polysaccharide-purifying method to obtain a high-purity product. For purification, various methods such as various types of column chromatography such as ion exchange, gel filtration, affinity, etc., precipitation by addition of quaternary ammonium salt, salting-out, precipitation by use of an organic solvent, etc., can be used.

The polymerization degree of the polysaccharides of the present invention can be varied by adjusting the operating conditions such as medium composition used for culture, polysaccharide-collecting method, etc. Also, the collected product or purified product may be hydrolyzed with TFA, formic acid, hydrochloric acid or the like and adjusting the hydrolysis conditions. Thus, the molecular weight of the polysaccharides of the present invention may be adjusted within the range of about $5 \times 10^3$ to $10 \times 10^6$.

The polysaccharides of the present invention have many useful properties such as water-retaining property, film-forming property, dispersion-stabilizing property, etc. as well as moisture-retaining property. Especially, with regard to the moisture-retaining property, it is noted that the polysaccharides of the present invention are less prone to be influenced by the ambient humidity than sodium hyaluronate which is a typical humectant. In terms of high moisture retaining performance, polysaccharides with a molecular weight of about $10^5$ to $10^6$ are preferably used.

The polysaccharides of the present invention are chemically more stable substance than sodium hyaluronate. The polysaccharides of the present invention (molecular weight: about $2 \times 10^6$), sodium hyaluronate derived from cockscomb (molecular weight: about $2 \times 10^6$) and sodium hyaluronate produced from microbial fermentation (molecular weight: about $2 \times 10^6$) were each dissolved at a concentration of 0.2% (w/v) in water, 0.1 M HCl and 0.1 M NaOH and kept in a sealed container at 50° C. for one month. The change of molecular weight after storage was examined by high-performance liquid chromatography. The results are shown in Table 2.

TABLE 2

| Solvent: | <Molecular weight after storage> | | |
|---|---|---|---|
| | Polysaccharide of the present invention | Sodium hyaluronate derived from cockscomb | Sodium hyaluronate produced from microbial fermentation |
| Water | $1.8 \times 10^6$ | $1.6 \times 10^6$ | $1.6 \times 10^6$ |
| 0.1 M HCl | $1.7 \times 10^4$ | $1.6 \times 10^4$ | $1.7 \times 10^4$ |
| 0.1 M NaOH | $1.2 \times 10^6$ | Perfectly decomposed | Perfectly decomposed |

As is seen from Table 2, the polysaccharides of the present invention and sodium hyaluronates from the said two sources maintain a molecular weight greater than $10^6$ when dissolved and kept in water, and each of their molecular weight is reduced to about 1/100 when dissolved and kept in 0.1 M HCl. However, when dissolved and kept in 0.1 M NaOH, sodium hyaluronates from the said two sources are decomposed to the constituent glycose unit, whereas the polysaccharide of the present invention still maintains a molecular weight above $10^6$. This fact shows that chemical stability of the polysaccharides of the present invention is higher than sodium hyaluronate.

Also, when the polysaccharides of the present invention are cast uniformly onto a flat plate as a 0.5% (w/v) aqueous solution and dried, a colorless transparent and tough film is formed. Such film forming property of the polysaccharides enables to use the polysaccharides as a material for packaging film or coating agent. Especially, a film obtained from the polysaccharides of the present invention from which O-acetyl groups are perfectly removed (less than 1 wt % based on the whole polysaccharide) by a deacetylation treatment is excellent in tensile strength and elongation at break.

Further, when the polysaccharides of the present invention are formed into a 0.2% (w/v) aqueous solution and heat treated, the solution viscosity is reduced to a similar level to that of water without any substantial change of molecular weight. Therefore, even if titanium oxide or the like is added to the aqueous solution of the polysaccharides of the present invention, sedimentation is prevented, like gum arabic or the like. Thus, the polysaccharides of the present invention are expected to be used as a low-viscosity dispersion stabilizer in place of gum arabic whose price has risen recently because of elevation of raw material cost. Its use as an emulsion stabilizer is also expected because of excellent emulsion stability for oils such as salad oil. Further, the polysaccharides of the present invention are usable as a foam stabilizer, a water-retaining agent and a cement admixture as mentioned in the Examples given below.

According to the present invention, it is possible to produce, at high efficiency, novel polysaccharides which can be used as a humectant, a film-forming agent, an emulsifier, a foam stabilizer, a water-retaining agent, a cement admixture, etc., in various fields with good compatibility with earth environment and, especially as a humectant, is free of the problems of the conventional products.

EXAMPLES

The present invention will be described in more detail below with reference to the examples, but it is to be understood that these examples are merely intended to be illustrative and not to be construed as limiting the scope of the invention.

Example 1

Preparation of polysaccharide

In a 500 ml Sakaguchi's flask, 100 ml of a medium of the following composition was placed. After autoclaving at 121° C. for 20 minutes, slant-cultured Azotobacter beijerinckii TNM1 (FERM BP-4194) was inoculated with a platinum loop and subjected to reciprocal shaking culture at 110 strokes per minutes at 28° C. for 3 days.

| Medium composition (wt %) | |
|---|---|
| Saccharose | 2% |
| Sodium nitrate | 0.2% |
| Dipotassium hydrogenphosphate | 0.1% |
| Magnesium sulfate heptahydrate | 0.05% |
| Potassium chloride | 0.05% |
| Iron sulfate heptahydrate | 0.001% |
| Yeast extract | 0.05% |
| pH | 6 |

Into a 10-liter jar fermentor containing 6 liters of a medium of the same composition as specified above and subjected to the same sterilization as described above, 60 ml of the resultant liquid culture was inoculated, and then submerged culture was conducted for 63 hours under the conditions of 28° C., 400 r.p.m. and 6 l/min of aeration. The resultant culture was diluted three-fold with water and then the bacterial cells were removed by centrifugation. The supernatant of the obtained liquid culture was subjected to repeated crossflow ultrafiltration until the substances (such as residual medium components) other than the polysaccharide of the present invention were removed. For ultrafiltration, an ultrafiltration system "UF-LMSII" (fraction molecular weight: $3\times10^6$; mfd. by Toso Co., Ltd.) was used. The concentrated solution which did not pass through the ultrafiltration membrane was freeze-dried to obtain about 3 g of homogeneous polysaccharide per liter of medium. Homogeneity of the polysaccharide was confirmed by GPC mode high-performance liquid chromatography.

Molecular weight of the obtained polysaccharide was measured by high-performance liquid chromatography with "Asahipak GFA-7MF" column (mfd. by Asahi Chemical Industry Co., Ltd.) using a 0.1M $NaNO_3$ aqueous solution as mobile phase. Retention time of the peak top on the chromatogram of the polysaccharide was of a value equivalent to a molecular weight of about $2\times10^6$ in the molecular weight-retention time standard curve drawn by using pullulans of a known molecular weight as standard.

Also, the carboxyl groups of uronic acids in the obtained polysaccharide were reduced and the resultant polysaccharide was hydrolyzed to the constituent glycoses. The constituent glycoses were fluorescent-labeled and subjected to liquid chromatographic analysis. The molar ratio of the constituent glycoses was determined from a previously prepared calibration curve and the peak heights of the respective constituent glycoses. The results showed as follows:

D-galacturonic acid:L-rhamnose:D-glucose=0.8:1.0:1.0.

The polysaccharide was subjected to partial hydrolysis with 0.25 M TFA at 100° C. for each of the periods of 3, 4, 5 and 6 hours, and then the alditol acetates were derived therefrom. Each of the obtained derivatives was subjected to gas chromatographic analysis using 3% ECNSS-M coated Gas Chrom Q column (mfd. by Wako Pure Chemical Industries, Ltd.). Regarding the peak areas of the derivatives from D-glucose and L-rhamnose on the chromatogram, the peak area was substantially constant regardless of the time of hydrolysis in the case of D-glucose, while the peak area increased with the time of hydrolysis in the case of L-rhamnose.

It is known that, generally, a linkage between the uronic acid residue and the neutral saccharide residue glycosidic-linked to carbon atom at the 1-position of the uronic acid residue in a polysaccharide is relatively stable to acids. It is therefore considered that the residue glycosidic-linked to carbon atom at the 1-position of D-galacturonic acid residue in the obtained polysaccharide is principally L-rhamnose residue.

For examining modification of hydroxyl group of the obtained polysaccharide, it was subjected to a deacylation treatment in the 0.01 M KOH and 0.13 M KCl aqueous solution at room temperature for 5 hours, and high-performance liquid chromatographic analysis was conducted on the treated sample. As a result, there was detected a peak having the same retention time as the peak which appeared in the analysis of potassium acetate aqueous solution. The O-acetyl group content of the polysaccharide was determined from the previously prepared calibration curve and its peak height. It was 6 wt % based on the whole polysaccharide. In the infrared absorption spectrum of the deacylated polysaccharide, the peak at around 1730 $cm^{-1}$ was disappeared.

Example 2

Preparation of polysaccharide

The procedure of Example 1 was followed except that the jar-fermentor was operated at a speed of 200 r.p.m. and that the culture was continued for 51 hours. As a result, there was obtained 1.3 g of homogeneous polysaccharide per liter of medium. The molar ratio of the constituent glycoses of the obtained polysaccharide was determined in the same way as Example 1: D-galacturonic acid:L-rhamnose:D-glucose= 1.0:1.1:1.0. The molecular weight of the polysaccharide was $2.6\times10^6$.

Example 3

Preparation of polysaccharide

In a 500 ml Sakaguchi's flask, 100 ml of a medium of the same composition as Example 1 was placed. After autoclaving at 121° C. for 20 minutes, slant-cultured Azotobacter beijerinckii TNM1 (FERM BP-4194) was inoculated with a platinum loop and subjected to reciprocal shaking culture at 110 strokes per minute at 28° C. for 5 days.

The obtained culture was diluted two-fold with water and then the bacterial cells were removed by centrifugation. To the supernatant of the thus obtained culture medium, three equivalents (v/w) of ethanol was added, and the produced precipitate was dissolved in water and dialyzed against running water for 2 days. The resulting dialyzate was freeze-dried to obtain 1.1 g of homogeneous polysaccharide per liter of medium. The molar ratio of the constituent glycoses of the obtained polysaccharide was determined in the same way as Example 1: D-galacturonic acid:L-rhamnose:D-glucose=0.7:0.8:1.0. The molecular weight of the polysaccharide was $3.0\times10^6$.

Example 4

Preparation of polysaccharide

The procedure of Example 3 was followed except for use of a medium having a composition of 4 wt % glucose, 0.2 wt % polypeptone, 0.1 wt % yeast extract and 0.1 wt % meat extract and a pH of 7. There was obtained 2.7 g of homogeneous polysaccharide per liter of medium. The molar ratio of the constituent glycoses of the obtained polysaccharide was determined in the same way as Example 1: D-galacturonic acid :L-rhamnose:D-glucose=0.6:1.2:1.0. The molecular weight of the polysaccharide was $1.9\times10^6$.

Example 5

Preparation of polysaccharide

The procedure of Example 1 was followed except that at 24 hours after start of submerged culture, the speed of the jar fermentor was raised to 800 r.p.m., and that the total culture time was 72 hours. There was obtained 6.6 g of homogeneous polysaccharide per liter of medium. The molar ratio of the constituent glycoses of the obtained polysaccharide, was determined in the same way as Example 1: D-galacturonic acid:L-rhamnose:D-glucose=0.7:0.7:1.0. The molecular weight of the polysaccharide was $2.3\times10^6$.

Example 6

Evaluation of moisture retainability of polysaccharide

The polysaccharide obtained in Example 1 (molecular weight: about $2\times10^6$) was put into a weighing tube. After dried in vacuo sufficiently, the polysaccharide was placed in a desiccator, which had been adjusted to 79% RH with $NH_4Cl$, and left therein until its weight became constant.

Then the polysaccharide was transferred into another desiccator which had been adjusted to 42% RH with $Zn(NO_3)_2 \cdot 6H_2O$, and left therein until its weight again became constant. The above operations were conducted at the fixed temperature of 20° C.

For comparison of moisture retaining property, the similar operation was carried out with sodium hyaluronate derived from cockscomb (molecular weight: about $2 \times 10^6$, produced by Cupie Corp.) and sodium hyaluronate produced from microbial fermentation (molecular weight: about $2 \times 10^6$, produced by Denki Kagaku Kogyo co., Ltd.).

The moisture retention under each of the RH conditions was calculated from the following equation. The result of evaluation of moisture retainability is shown in Table 3.

$$Moisture\ retention\ (\%) = (A-B)/B \times 100$$

A: sample weight when it became constant under each of the RH conditions
B: dry sample weight

TABLE 3

| | <Moisture retention %> | | |
|---|---|---|---|
| | Polysaccharide of the present invention | Sodium hyaluronate derived from cockscomb | Sodium hyaluronate produced from microbial fermentation |
| 79% RH | 31 | 45 | 42 |
| 42% RH | 24 | 30 | 30 |
| Difference | 7 | 15 | 12 |

As is seen from the above results, any of the test compounds shows the generally required level of moisture retention (10–50%) under the ordinary environmental condition of 40–80% RH. However, the influence by change of relative humidity, namely the difference in moisture retention at 79% RH and that at 42% RH is 15% in the case of sodium hyaluronate derived from cockscomb and 12% in the case of sodium hyaluronate produced from microbial fermentation, whereas such difference is only 7% in the case of the polysaccharide of the present invention. Thus, a humectant composed of the polysaccharide of the present invention is superior to those composed of the said types of sodium hyaluronate in that the former is less susceptible to change of relative humidity.

Example 7

Evaluation of film-forming property of polysaccharide

The polysaccharide (molecular weight: about $2 \times 10^6$) obtained in Example 1 was subjected to a deacetylation treatment in the 0.01M KOH and 0.13M KCl aqueous solution at room temperature for 5 hours, then neutralized, dialyzed against water and freeze-dried to obtain a deacetylated polysaccharide (O-acetyl group content: less than 0.1 wt %).

The aqueous solutions prepared by dissolving the above deacetylated polysaccharide and the polysaccharide obtained in Example 1 in water to have a concentration of 1% (w/v) were cast into a mold placed on a PET sheet and then dried at 50° C. to make the film-like moldings. For the sake of comparison, a similar film-like molding was made by using pullulan ("Pullulan PI-20" produced by Hayashibara Co., Ltd.) in the above procedure.

Tensile strength and elongation at break of the obtained film-like moldings were measured by using a precision universal testing machine (AGS-500B mfd. by Shimadzu Corp.). The results are shown in Table 4.

TABLE 4

| | Polysaccharide of the present invention | Deacetylated polysaccharide of the present invention | Pullulan |
|---|---|---|---|
| Tensile strength ($kg/cm^2$) | 255 | 560 | 500 |
| Elongation at break (%) | 6 | 21 | 3 |

As is evident from the above results, the film-like moldings obtained from the polysaccharide of the present invention have practically sufficient tensile strength and elongation at break. It is remarkable that the film-like molding obtained from the deacetylated polysaccharide of the present invention has higher tensile strength and elongation at break.

Example 8

Evaluation of emulsion-stabilizing effect of polysaccharide

To 35 g of an aqueous solution prepared by dissolving the polysaccharide (molecular weight: about $2 \times 10^6$) obtained in Example 1 in water to have a concentration of 1% (w/v), the equal amount (w/w) of salad oil was added gradually with stirring by a homomixer at 10,000 r.p.m. After addition of salad oil was completed, the mixed solution was further stirred for 5 minutes to form an emulsion and then allowed to stand as it was. For the sake of comparison, a similar preparation was obtained by using carrageenan (trade name: CP Gum FA, produced by Dai-Nippon Pharmaceutical Co., Ltd.) in the above procedure.

In both cases of the polysaccharide of the present invention and carrageenan, there was formed a white creamy emulsion immediately after emulsification. However, in the case of carrageenan, an aqueous phase was observed after 24-hour standing, and this aqueous phase held about 3/10 of the whole height of the solution after 120-hour standing. In contrast, in the case of the polysaccharide of the present invention, there was observed no phase separation even after 120-hour standing. This indicates that the polysaccharide of the present invention has better emulsion-stabilizing effect to salad oil than carrageenan. The similar result was obtained with the deacetylated polysaccharide of the present invention.

Example 9

Evaluation of foam-stabilizing effect of polysaccharide in milk

One (1) g of the polysaccharide obtained in Example 5 was added to 100 ml of cow's milk and stirred by a homomixer at 10,000 r.p.m. to generate foams. For the comparison's sake, the same operation was carried out by using carrageenan (CP Gum FA, Dai-Nippon Pharmaceutical Co., Ltd.). In the case of the polysaccharide of the present invention, there took place a volume increment of 30%, but in the case of carrageenan, the volume increment was 10%. Also, in the case of carrageenan, foams disappeared after 24-hour standing, but in the case of the polysaccharide of the present invention, foams still existed in a stable form.

Example 10

Evaluation of foam-stabilizing effect of polysaccharide in ice-cream

First, 1,000 g of cow's milk was put into a 3-liter stainless steel vat and stirred with the vat kept in a 70° C. water bath. Then a mixture of 120 g of skim milk powder, 130 g of sugar and 5 g of the polysaccharide obtained in Example 5 was added to the milk with stirring, followed by further addition of 250 g of whole condensed milk, 200 g of raw cream (milk fat content: 40%), 100 g of yolk and 2 g of vanilla essence successively to prepare a mix. This mix was kept at 80° C. for 10 minutes, then homogenized and frozen. At the point when temperature reached −3° C., sampling was made to obtain a vanilla ice cream sample with a milk fat content of 14.0% and a nonfat milk solid content of 13.0%. For the sake of comparison, a similar ice cream sample was obtained by carrying out the same operation except for use of 5 g of carrageenan (CP Gum FA) in place of the polysaccharide of the present invention.

Determination was made of overrun for each of the ice cream samples. Overrun was calculated from measurements of weight of 100 ml of the mix immediately before freezing and 100 ml of ice cream immediately after freezing. A 100 ml plastic container was used for measurement of weight. Overrun of the ice cream using carrageenan was 35% while that of the ice cream using the polysaccharide of the present invention was 50%.

Example 11

Evaluation of water retainability of polysaccharide in sponge cake

The polysaccharide obtained in Example 5 was added to a cake mix so that the polysaccharide content became 0.5 wt %, then water was added thereto to prepare a dough and it was baked in an oven. For the sake of comparison, the same operation was repeated except for use of 0.5 wt % of carrageenan (CP Gum FA) in place of the polysaccharide to obtain a sponge cake. The amount of water released in 24-hour standing at −20° C. was measured. Water release rate was 2% in the sponge cake containing the polysaccharide of the present invention and 10% in the sponge cake containing carrageenan.

Example 12

Evaluation of thickening and water retaining effects of polysaccharide in cement Fifty (50) g of Portland cement (produced by Sumitomo Cement Co., Ltd.) was added to each of (1) 25 ml of a 0.4% (w/v) aqueous solution of the polysaccharide obtained in Example 9, (2) 25 ml of a 0.1M NaOH aqueous solution containing 1 wt % (w/v) of curdlan (Wako Pure Chemical Industries, Ltd.) and (3) 25 ml of water, and mixed by stirring. 20 g of each of the thus prepared cement slurries was put into a plastic laboratory dish (90 mm in diameter and 15 mm high) and the dish was vibrated to let the slurry spread over the entirety of the dish. Immediately thereafter, the dish was raised vertically and left as it was, allowing the cement therein to set. The operation was carried out at room temperature. After the cement has set, thickness of the set cement at the upper, middle and lower portions of the dish was measured. The results are shown in Table 5. It is seen from the results of Table 5 that it is possible to prevent run-down of the cement slurry by adding the polysaccharide of the present invention.

TABLE 5

|  | Upper portion (mm) | Middle portion (mm) | Lower portion (mm) |
| --- | --- | --- | --- |
| Set cement containing polysaccharide | 3 | 3 | 3 |
| Set cement containing curdlan | 3 | 3 | 6 |
| set cement containing no additive | 2 | 2 | 10 |

Example 13

Property-improving effect of polysaccharide in hydraulic compositions

There were prepared hydraulic compositions of the formulations shown in Table 6, in which the polysaccharide obtained in Example 5 and curdlan (produced by Wako Pure Chemical Industries, Ltd.) were blended respectively. The slump flow value, which is an index of fluidity, and compression strength of the compositions when worked into reinforced concrete were measured. The results are shown in Table 6. Reinforced concrete was made by placing concrete in a mold where the reinforcing bars were arranged at minimum intervals of 35 mm, and compression strength was measured 6 days, 7 days and 28 days after production of concrete. The results given in Table 6 show that the properties of the hydraulic compositions can be improved by adding the polysaccharide of the present invention. The figures in the parentheses in the table are % by weight based on the binders (cement, blast-furnace slag and fly ash). The "high-performance water-reducing agent" is a naphthalene-sulfonic acid-formalin high condensate, and the AE water-reducing agent" is a lignosulfonic acid compound-polyol complex.

TABLE 6

|  | Cement blended with polysaccharide of the present invention | Cement blended with curdlan |
| --- | --- | --- |
| <Amount (wt %)> |  |  |
| Water | 150 | 150 |
| Cement | 150 | 150 |
| Blast-furnace slag | 150 | 150 |
| Fly ash | 200 | 200 |
| Fine aggregate | 660 | 660 |
| Coarse aggregate (max. size: 20 mm) | 940 | 940 |
| High-performance water-reducing agent | 5 (1) | 5 (1) |
| AE water-reducing agent | 0.75 (0.15) | 0.75 (0.15) |
| Polysaccharide | 1.5 (0.3) | 0 |
| Curdlan | 0 | 1.5 (0.3) |
| Slump flow value (cm) | 50 | 48 |
| Compression strength |  |  |

TABLE 6-continued

| | Cement blended with polysaccharide of the present invention | Cement blended with curdlan |
|---|---|---|
| (kgf/cm$^2$) Age of cement: | | |
| 6 days | 286 | 285 |
| 7 days | 287 | 286 |
| 28 days | 428 | 427 |

What is claimed is:

1. Polysaccharides having the following physicochemical properties:
   (1) a molecular weight determined by gel filtration chromatography is about $5 \times 10^3$ to $10 \times 10^6$,
   (2) the constituent glycoses are D-galacturonic acid, L-rhamnose and D-glucose,
   (3) the constituent glycoses are joined substantially by 1,3-linkages, and
   (4) a configuration of D-galacturonic acid is α, that of L-rhamnose is β and that of D-glucose is α.

2. Polysaccharides according to claim 1, wherein a molar ratio of the constituent glycoses is: D-galaturonic acid:L-rhamnose:D-glucose=0.6–1.0:0.8–1.2:0.8–1.2.

3. A humectant comprising polysaccharides which has a molecular weight determined by gel filtration chromatography is about $5 \times 10^3$ to $10 \times 10^6$ and which is composed of D-galacturonic acid, L-rhamnose and D-glucose.

4. A humectant according to claim 3, wherein the constituent glycoses are joined substantially by 1,3-linkages, and a configuration of D-galacturonic acid is α, that of L-rhamnose is β and that of D-glucose is α.

5. A humectant according to claim 3, wherein a molar ratio of the constituent glycoses is: D-galacturonic acid:L-rhamnose:D-glucose=0.6–1.0:0.8–1.2:0.8–1.2.

6. A humectant according to claim 4, wherein a molar ratio of the constituent glycoses is: D-galacturonic acid:L-rhamnose:D-glucose=0.6–1.0:0.8–1.2:0.8–1.2.

7. A film forming agent comprising polysaccharides which have a molecular weight determined by gel filtration chromatography is about $5 \times 10^3$ to $10 \times 10^6$ and which is composed of D-galacturonic acid, L-rhamnose and D-glucose.

8. An emulsion stabilizer comprising polysaccharides which have a molecular weight determined by gel filtration chromatography is about $5 \times 10^3$ to $10 \times 10^6$ and which is composed of D-galacturonic acid, L-rhamnose and D-glucose.

9. A foam stabilizer comprising polysaccharides which have a molecular weight determined by gel filtration chromatography is about $5 \times 10^3$ to $10 \times 10^6$ and which is composed of D-galacturonic acid, L-rhamnose and D-glucose.

10. A water-retaining agent comprising polysaccharides which have a molecular weight determined by gel filtration chromatography is about $5 \times 10^3$ to $10 \times 10^6$ and which is composed of D-galacturonic acid, L-rhamnose and D-glucose.

11. A cement admixture comprising polysaccharides which have a molecular weight determined by gel filtration chromatography is about $5 \times 10^3$ to $10 \times 10^6$ and which is composed of D-galacturonic acid, L-rhamnose and D-glucose.

* * * * *